United States Patent [19]

Hegasy et al.

[11] Patent Number: 4,857,312
[45] Date of Patent: Aug. 15, 1989

[54] DIHYDROPYRIDINE SPRAY, PROCESS FOR ITS PREPARATION AND ITS PHARMACEUTICAL USE

[75] Inventors: Ahmed Hegasy, Leverkusen; Klaus-Dieter Rämsch, Wuppertal, both of Fed. Rep. of Germany

[73] Assignee: Bayer Aktiengesellschaft, Leverkusen, Fed. Rep. of Germany

[21] Appl. No.: 169,566

[22] Filed: Mar. 17, 1988

Related U.S. Application Data

[63] Continuation of Ser. No. 942,479, Dec. 15, 1986, abandoned.

[30] Foreign Application Priority Data

Dec. 18, 1985 [DE] Fed. Rep. of Germany ....... 3544692

[51] Int. Cl.⁴ ...................... A61K 31/44; A61K 31/79
[52] U.S. Cl. ........................ 424/80; 514/338; 514/344; 514/356
[58] Field of Search ................ 424/80, 338; 514/356, 514/344

[56] References Cited

U.S. PATENT DOCUMENTS

| | | | |
|---|---|---|---|
| 3,784,684 | 1/1974 | Bossert et al. | |
| 3,920,823 | 11/1975 | Meyer et al. | 514/356 |
| 4,166,855 | 9/1979 | Wehinger et al. | 514/356 |
| 4,364,952 | 12/1982 | Materne | 514/356 |
| 4,537,898 | 8/1985 | Hoff et al. | 514/356 |
| 4,582,840 | 4/1986 | Garthoff et al. | 514/356 |
| 4,607,041 | 8/1986 | Baxter et al. | 514/338 |
| 4,621,093 | 11/1986 | Ulrich et al. | 514/356 |

FOREIGN PATENT DOCUMENTS 3316510  11/1984  Fed. Rep. of Germany ...... 514/356

Primary Examiner—Allen J. Robinson
Attorney, Agent, or Firm—Sprung Horn Kramer & Woods

[57] ABSTRACT

A sprayable liquid formulation comprising, per 100 ml of the formulation, (a) 0.2 to 5 grams of a dihydropyridine of the formula

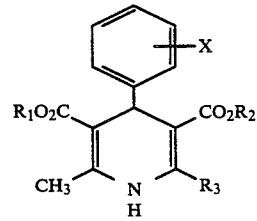

in which
$R^1$ and $R^2$ each independently is alkyl with 1 to 10 carbon atoms optionally substituted by alkoxy with 1 to 3 carbon atoms, trifluoromethyl, halogen or N-methyl-N-benzylamino,
$R^3$ is alkyl with 1 to 4 carbon atoms, cyano or hydroxymethyl, and
X is a nitro group, one or two chlorine groups or the ring member =N—O—N=, (b) 10 to 40 grams of polyethylene glycol with an average molecular weight of 200 to 600,
(c) 25 to 60 grams of ethyl alcohol, and
(d) 3 to 15 grams of polyvinylpyrrolidine with an average molecular weight of 12000 to 30000.

8 Claims, No Drawings

DIHYDROPYRIDINE SPRAY, PROCESS FOR ITS PREPARATION AND ITS PHARMACEUTICAL USE

This is a continuation of application Ser. No. 942,479 filed Dec. 15, 1986 now abandoned.

The invention relates to sprayable liquid formulations of dihydropyridines, processes for their preparation and their use in combating diseases.

The dihydropyridines which can be used according to the invention and their potent circulation-influencing actions are widely known (compare British Pat. No. 1,173,862 and British Pat. No. 1,358,951). It is also known that these dihydropyridines have only a very low solubility, which, for example, is only about 6 to 10 mg/l of water for nifedipine. Because of this poor solubility and, in particular, their high photosensitivity, a number of difficulties arise when they are processed galenically. The photosensitivity of some nitrophenyl substituted dihydropyridines is so high, especially in the dissolved form, that under the action of daylight the active compound is already converted completely into inactive decomposition products after a few minutes.

Liquid formulation forms which, however, are not suitable for use as a spray are already known for some dihydropyridines. In U.S. Pat. No. 3,784,684, for example, soft gelatine capsules with a liquid filling are described. These nifedapine solutions, however, are unsuitable for spraying, since they have a high viscosity and can block the nozzles of the spray device. DE-OS (German Published Specification) 3,307,422 likewise describes solutions of dihydropyridines which contain diluents and solubilizing agents. However, these liquid formulations are unsuitable as an oral spray, since they cause irritation of the mucous membrane in the pharingeal region and lead to coughing fits and difficult breathing. German Offenlegungschriften (German Published Specifications) No. 3,315,805 and 3,339,239 also describe liquid dihydropyridine formulations in the form of emulsions. These emulsions are likewise unsuitable as a spray and do not display a sufficiently rapid action when they come into contact with the mucous membranes of the pharynx and of the respiratory system.

All previous attempts to compensate the poor solubility of dihydropyridines by certain measures and at the same time to provide a rapidly acting formulation form which is tolerated well have so far not led to satisfactory results. There is therefore a need to provide a well-tolerated formulation of the highly active dihydropyridines, which guarantees the fastest possible onset of action, a high bioavailability and simple use. An even more rapid onset of action than that of the previously known soft gelatine capsules containing nifedapine is desirable in many cases. The known drop formulations containing nifedipine are inferior to the spray formulations according to the invention in respect of their handling and their dosage accuracy.

The invention relates to sprayable liquid formulations of dihydropyridines of the general formula (I)

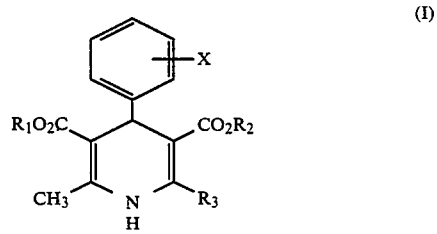

in which
R[1] and R[2] are identical or different and each represent alkyl with 1 to 10 carbon atoms, in particular 1 to 4 carbon atoms, optionally substituted by alkoxy with 1 to 3 carbon atoms, trifluoromethyl, halogen or N-methyl-N-benzylamino, R[3] represents alkyl with 1 to 4 carbon atoms, cyano or hydroxymethyl and X represents a nitro group, one or two chlorine groups or the ring member =N—O—N=, characterized in that they contain (a) 0.2 to 5 parts by weight of dihydropyridines per 100 parts by volume of liquid formulation, (b) 10 to 40 parts by weight of polyethylene glycol with an average molecular weight of 200 to 600 per 100 parts by volume of liquid formulation, (c) 25 to 60 parts by weight of ethyl alcohol per 100 parts by volume of liquid formulation, (d) 3 to 15 parts by weight of polyvinylpyrrolidone with an average molecular weight of 12000 to 30000 per 100 parts by volume of liquid formulation, and (e) if appropriate also other inert auxiliaries, such as 2 to 25 parts by weight of glycerol or water or mixtures thereof, light-stabilizing dyestuffs which are tolerated well, such as β-carotene (E160a) or orange-yellow S (E110), and small amounts of agents which improve the flavor, such as sweeteners, essential oils or aromas.

Parts by weight are grams or kilograms, which correspond to the parts by volume of milliliters or liters.

These sprayable liquid formulations according to the invention represent presentation forms which are easy to handle, function reliably, have a rapid action, are readily absorbed and are tolerated well. A particular advantage is their good local tolerance on the mucous membrane of the pharynx.

Preferred dihydropyridines which may be mentioned are the compounds in the following table.

TABLE

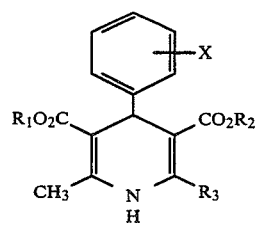

| No. | X | R¹ | R² | R³ | Generic |
|---|---|---|---|---|---|
| 1 | 2-$NO_2$ | $CH_3$ | $CH_3$ | $CH_3$ | nifedipine |
| 2 | 3-$NO_2$ | $nPrOCH_2CH_2$ | $nPrOCH_2CH_2$ | $CH_3$ | niludipine |
| 3 | 3-$NO_2$ | $C_2H_5$ | $CH_3$ | $CH_3$ | nitrendipine |
| 4 | 2-$NO_2$ | $CH_3$ | $(CH_3)_2CHCH_2$ | $CH_3$ | nisoldipine |
| 5 | 3-$NO_2$ | $CH(CH_3)_2$ | $(CH_2)_2-O-CH_3$ | $CH_3$ | nimodipine |
| 6 | 3-$NO_2$ | $C_2H_5$ | $C_{10}H_{21}(n)$ | $CH_3$ | |
| 7 | 2-Cl | $CH_3$ | $CH_2-CF_3$ | $CH_3$ | |
| 8 | 2-Cl | $C_2H_5$ | $CH_2-CF_3$ | $CH_3$ | |
| 9 | 3-$NO_2$ | $CH(CH_3)_2$ | $n\text{-}PrO-CH_2CH_2$ | $CH_3$ | |
| 10 | 3-$NO_2$ | $CH_3$ | $C_6H_5CH_2N(CH_3)CH_2CH_2$ | $CH_3$ | nicardipine |
| 11 | 2,3-$Cl_2$ | $C_2H_5$ | $CH_3$ | $CH_3$ | f-lodipine |
| 12 | 2,3=N—O—N= | $C_2H_5$ | $C_2H_5$ | $CH_3$ | |
| 13 | 2,3=N—O—N= | $CH_3$ | $CH(CH_3)_2$ | $CH_3$ | |
| 14 | 3-$NO_2$ | $C_2H_5$ | $C_2H_5$ | $CH_2OH$ | |
| 15 | 3-$NO_2$ | $CH_3$ | $CH_3$ | CN | | n-Pr = n-propyl

Compounds 1, 3, 4 and 5 in the table may be mentioned as preferred.

A preferred embodiment comprises liquid formulations containing (a) 0.5 to 4 parts by weight of dihydropyridine, (b) 15 to 30 parts by weight of polyethylene glycol of average molecular weight 400, (c) 30 to 50 parts by weight of ethyl alcohol, (d) 4 to 10 parts by weight of polyvinylpyrrolidone and, if appropriate, (e) 5 to 18 parts by weight of glycerol or water or a mixture of glycerol and water.

Preferred light-stabilizing dyestuffs which may be mentioned are:

β-carotene (E160a) and its water-soluble dispersions, orange-yellow S (E110) and/or quinoline yellow (E102).

A concentration is in each case 0.01 to 0.5 part by weight, preferably 0.1 to 0.4 part by weight, based on the volume of the liquid formulation.

Preferred flavor correctants which may be mentioned are: sweeteners, such as sodium saccharin or sodium cylamate, and essential oils, such as peppermint oil.

They are preferably employed in amounts of 0.01 to 0.5 part by weight.

The spray solution according to the invention is prepared by dissolving 0.2 to 5 parts by weight of the dihydropyridine in 10 to 40 parts by weight of the polyethylene glycol and 25 to 60 parts by weight of the ethanol, and subsequently adding 3 to 15 parts by weight of the polyvinylpyrrolidone and, if appropriate, further auxiliaries and then bringing the pH value of the solution to about 6.5 to 7.5. Alternatively, the polyvinylpyrrolidone can be dissolved in a portion of the water and this solution can be added to the dihydropyridine solution. The resulting solution is introduced into bottles, which are preferably equipped with a pump metered-spray attachment.

The piston volume of the pump metered-spray attachment can be varied and is preferably 0.1 to 0.5 ml, so that corresponding dihydropyridines can be administered in dosages of 0.2 to 25 mg per single puff.

EMBODIMENT EXAMPLES

Example 1

28 g of nifedipine are dissolved in a mixture of 450 g of ethanol and 300 g of polyethylene glycol 400. 75 g of polyvinylpyrrolidine and 4 g of orange-yellow S are separately dissolved in 115 g of water and the solution is added to the nifedipine solution. The resulting solution is introduced into bottles fitted with a pump metered-spray attachment with a piston volume of 0.18 ml. An oral spray containing 5 mg of nifedipine is obtained per puff.

Example 2

20 g of nifedipine are dissolved in 450 g of ethanol and 250 g of polyethylene glycol 400. 70 g of polyvinylpyrrolidone 25 and 2 g of sodium saccharin are separately dissolved in 121 g of water and the solution is then added to the nifedipine solution. 50 g of anhydrous glycerol and 2 g of peppermint oil are then added. The pH value of the solution is brought to about 7 with sodium hydroxide solution. The solution is filtered and introduced into containers with a pump metered-spray attachment with a stroke volume of 0.25 ml. 5 g of nifedipine are administered per puff.

Example 3

A solution which additionally contains 0.001% of β-carotene is prepared analogously to Example 2.

Example 4

A solution which additionally contains 0.4% of orange-yellow S is prepared analogously to Example 2.

Example 5

8 g of nisoldipine are dissolved in a mixture of 450 g of ethanol and 250 g of polyethylene glycol 400. 56 g of polyvinylpyrrolidine 25 and 2 g of sodium saccharin are dissolved separately in 132 g of water and the solution is added to the nisoldipine solution.

50 g of glycerol and 2 g of peppermint oil are then added. The pH value is brought to about 7 with sodium hydroxide solution. After filtration, the solution is introduced into containers with a pump metered-spray attachment with a volume of 0.125 ml. 1 puff gives 1 mg of nisoldipine.

Example 6

The solution analogous to Example 5 is introduced into containers with a pump metered-spray attachment with a stroke volume of 0.25 ml. 1 puff of this medicament form gives 2 mg of nisoldipine.

Example 7

16 g of nitrendipine are dissolved in a mixture of 480 g of ethanol, 200 g of polyethylene glycol 600 and 64 g of polyvinylpyrrolidones of molecular weight 25000. 100 g of a 70% strength aqueous sorbitol solution and 96 g of water are added to the solution. The solution is introduced into containers with a pump metered-spray attachment with a stroke volume of 0.25 ml. 4 mg of nitrendipine are administered to the patient per puff.

Example 8

Analogously to Example 2, 40 g of nimodipine are dissolved in 500 g of ethanol and 200 g of polyethylene glycol 400. 8 g of polyvinylpyrrolidine 25 are dissolved separately in 83 g of water and the solution is then added to the nimodipine solution. 40 g of anhydrous glycerol and 2 g of peppermint oil are then added. The solution is filtered and bottled. In each case 10 mg of nimodipine are administered with a stroke volume of 0.25 ml.

It is understood that the specification and examples are illustrative but not limitative of the present invention and that other embodiments within the spirit and scope of the invention will suggest themselves to those skilled in the art.

We claim:

1. A sprayable liquid formulation comprising, per 100 ml of the formulation,
    (a) 0.5 to 4 grams of a dihydropyridine of the formula

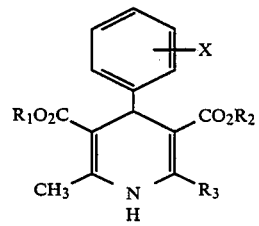

in which
    $R^1$ and $R^2$ each independently is alkyl with 1 to 10 carbon atoms optionally substituted by alkoxy with 1 to 3 carbon atoms, trifluoromethyl, halogen or N-methyl-N-benzylamino,
    $R^3$ is alkyl with 1 to 4 carbon atoms, cyano or hydroxymethyl, and
    X is a nitro group, one or two chlorine groups or the ring member =N—O—N=,
    (b) 15 to 30 grams of polyethylene glycol with an average molecular weight of 400,
    (c) 30 to 60 grams of ethyl alcohol, and
    (d) 4 to 20 grams of polyvinylpyrrolidine with an average molecular weight of 12000 to 30000.

2. A formulation according to claim 1, additionally containing from 2 to 25 grams, per 100 ml of the formulation, of glycerol or aqueous glycerol.

3. A formulation according to claim 1, additionally containing 0.01 to 0.5 grams, per 100 ml of the formulation, of β-carotene (E160a) or orange-yellow S (E110) as a light stabilizing dyestuff.

4. A formulation according to claim 1, wherein the dihydropyridine is selected from the group consisting of nifedipine, nisoldipine, niludipine, nitrendipine, nimodipine and felodipine.

5. A formulation according to claim 1, wherein the dihydropyridine is selected from the group consisting of nisoldipine, nitrendipine and nimodipine.

6. A formulation according to claim 5, wherein the dihydropyridine is selected from the group consisting of nifedipine, nisoldipine and nimodipine.

7. A formulation according to claim 5, additionally containing from 5 to 18 grams of glycerol or water or a mixture of glycerol and water.

8. A method for dihydropyridine therapy which comprises administering by spraying to a patient in need thereof a therapeutically effective amount of a composition according to claim 1.

* * * * *

UNITED STATES PATENT AND TRADEMARK OFFICE
CERTIFICATE OF CORRECTION

PATENT NO. : 4,857,312

DATED : August 15, 1989

INVENTOR(S) : Ahmed Hegasy

It is certified that error appears in the above-identified patent and that said Letters Patent is hereby corrected as shown below:

Col. 6, line 24 delete "20" before "grams" and substitute --10--

Signed and Sealed this

First Day of January, 1991

Attest:

HARRY F. MANBECK, JR.

*Attesting Officer*         *Commissioner of Patents and Trademarks*